(12) United States Patent
Kawas

(10) Patent No.: US 11,164,658 B2
(45) Date of Patent: Nov. 2, 2021

(54) IDENTIFYING SALIENT FEATURES FOR INSTANCES OF DATA

(71) Applicant: International Business Machines Corporation, Armonk, NY (US)

(72) Inventor: Ban Kawas, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 164 days.

(21) Appl. No.: 16/424,238

(22) Filed: May 28, 2019

(65) Prior Publication Data

US 2020/0381084 A1 Dec. 3, 2020

(51) Int. Cl.
  *G06T 7/00* (2017.01)
  *G16B 40/20* (2019.01)
  *G06N 20/00* (2019.01)
  *G06K 9/62* (2006.01)

(52) U.S. Cl.
  CPC .......... *G16B 40/20* (2019.02); *G06K 9/6247* (2013.01); *G06N 20/00* (2019.01); *G06T 7/0012* (2013.01)

(58) Field of Classification Search
  CPC .......... G06K 9/00335; G06K 9/00751; G06K 9/6215; G06T 7/0012
  See application file for complete search history.

(56) References Cited

U.S. PATENT DOCUMENTS

| 6,587,575 | B1 | 7/2003 | Windham et al. |
| 2002/0192686 | A1* | 12/2002 | Adorjan .............. C12Q 1/6883 435/6.12 |
| 2010/0312486 | A1 | 12/2010 | Khan et al. |
| 2011/0311129 | A1* | 12/2011 | Milanfar ............ G06K 9/00335 382/154 |
| 2017/0069113 | A1* | 3/2017 | Alpert ....................... G06T 7/90 |
| 2018/0254064 | A1* | 9/2018 | Gonzalez-Banos ......................... G11B 27/031 |
| 2019/0253614 | A1* | 8/2019 | Oleson ............. H04N 5/232935 |

FOREIGN PATENT DOCUMENTS

| CN | 107273917 A | 10/2017 |
| CN | 108763305 A | 11/2018 |
| CN | 109002859 A | 12/2018 |

OTHER PUBLICATIONS

Beilsmith, Kathleen, et al. "Genome-wide association studies on the phyllosphere microbiome: Embracing complexity in host-microbe interactions." The Plant Journal 97.1 (2019): 164-181. (Year: 2019).*

(Continued)

*Primary Examiner* — Li Liu
(74) *Attorney, Agent, or Firm* — Zilka-Kotab, P.C.

(57) ABSTRACT

A computer-implemented method according to one embodiment includes identifying principal components for a dataset defined by data instances and features corresponding to the data instances, identifying, for at least one of the data instances, at least some of the principal components, wherein the identified principal components are determined to be salient for said at least one data instance, and determining, for said at least one of the data instances, one or more salient features corresponding to the identified salient principal components.

24 Claims, 10 Drawing Sheets

(56) References Cited

OTHER PUBLICATIONS

Li, Jianke, Baojun Zhao, and Hui Zhang. "Face recognition based on PCA and LDA combination feature extraction." 2009 First International Conference on Information Science and Engineering. IEEE, 2009.*

Wang et al., "Knowledge-guided gene ranking by coordinative component analysis," BMC Bioinformatics, vol. 11, No. 162, 2010, pp. 1-13.

Stoyanova et al., "Normalization of single-channel DNA array data by principal component analysis," Bioinformatics, vol. 20, No. 11, Mar. 22, 2004, pp. 1772-1784.

Li et al., "Incorporating biological information in sparse principal component analysis with application to genomic data," BMC Bioinformatics, vol. 18, No. 332, 2017, pp. 1-12.

Lu et al., "Feature Selection Using Principal Feature Analysis," ACM, Multimedia, Sep. 2007, 4 pages.

Wikipedia, "Feature selection," Wikipedia, Apr. 26, 2019, 15 pages, retrieved from https://en.wikipedia.org/wiki/Feature_selection.

Kassambara, "Principal Component Methods in R: Practical Guide," STHDA, Sep. 23, 2017, 52 pages, retrieved from http://www.sthda.com/english/articles/31-principal-component-methods-in-r-practical-guide/112-pca-principal-component-analysis-essentials/.

* cited by examiner

FIG. 10

| | A | B | C | D | E | F | G | H | I | J | K |
|---|---|---|---|---|---|---|---|---|---|---|---|
| | Contamination | 1 | 0 | 1 | 0 | 0 | 0 | 0 | 0 | 1 | 0 |
| | OTUs\Samples | Sample 1 | Sample 2 | Sample 3 | Sample 4 | Sample 5 | Sample 6 | Sample 7 | Sample 8 | Sample 9 | Sample 10 |
| 529 | | | | | | | | | | | |
| 530 | | 0.0122652 | 0.0031175 | 0.0148166 | 0.0039537 | 0.0270944 | 0.0304632 | 0.0039229 | 0.0161839 | 0 | 0.0375494 |
| 531 | | 0.030662999 | 0.0031175 | 0.0037041 | 0.0039537 | 0.0033668 | 0 | 0.0039229 | 0.0121379 | 0.0040147 | 0.0041722 |
| 532 | | 0 | 0.0124699 | 0 | 0.0672135 | 0.0745097 | 0.0304932 | 0.0078458 | 0.0202299 | 0 | 0.0083443 |
| 533 | | 0.916823677 | 0.2681034 | 1.6520488 | 1.1584444 | 0.6536529 | 0.3467461 | 0.0902272 | 0.8941617 | 0.051861 | 1.2182684 |
| 534 | | 0.634724084 | 0.3055131 | 0.8852907 | 0.6484126 | 0.4436712 | 0.5067828 | 0.2902963 | 0.4936096 | 0.4777537 | 0.8970127 |

IDENTIFYING SALIENT FEATURES FOR INSTANCES OF DATA

BACKGROUND

The present invention relates to data analysis, and more specifically, this invention relates to analyzing data in order to determine salient features for that data.

Observed data are often analyzed in order to obtain a greater understanding of the observed data. For example, salient features of the observed data that best characterize such data are often sought in order to more efficiently label, organize, and utilize the data. However, there are currently no methods for efficiently and effectively determining salient features for observed data without given labels or annotations.

SUMMARY

A computer-implemented method according to one embodiment includes identifying principal components for a dataset defined by data instances and features corresponding to the data instances, identifying, for at least one of the data instances, at least some of the principal components, wherein the identified principal components are determined to be salient for said at least one data instance, and determining, for said at least one of the data instances, one or more salient features corresponding to the identified salient principal components.

According to another embodiment, a computer program product for identifying salient features for instances of data includes a computer readable storage medium having program instructions embodied therewith, where the computer readable storage medium is not a transitory signal per se, and where the program instructions are executable by a processor to cause the processor to perform a method including identifying, by the processor, principal components for a dataset defined by data instances and features corresponding to the data instances, identifying, by the processor for at least one of the data instances, at least some of the principal components, wherein the identified principal components are determined to be salient for said at least one data instance, and determining, by the processor for said at least one of the data instances, one or more salient features corresponding to the identified salient principal components.

According to another embodiment, a system includes a processor, and logic integrated with the processor, executable by the processor, or integrated with and executable by the processor, where the logic is configured to identify principal components for a dataset defined by data instances and features corresponding to the data instances, identify, for at least one of the data instances, at least some of the principal components, wherein the identified principal components are determined to be salient for said at least one data instance, and determine, for said at least one of the data instances, one or more salient features corresponding to the identified salient principal components.

According to another embodiment, a computer-implemented method includes identifying features found in at least one data instance, applying principal component analysis (PCA) to a dataset defined by a plurality of data instances including the at least one data instance and features corresponding to the at least one data instance to create at least one principal component for the at least one data instance, identifying, for the at least one data instance, a subset of at least one principal component, the subset indicating at least one principal component that is determined to be salient for the at least one data instance, determining, for the at least one data instance, a subset of the features, based on the subset of the principal components for the at least one data instance, the subset of the features indicating features that are determined to be salient for the at least one data instance, and performing one or more actions associated with the at least one data instance, utilizing the subset of the features determined to be salient for the at least one data instance.

According to another embodiment, a computer program product for identifying salient features for instances of data includes a computer readable storage medium having program instructions embodied therewith, where the computer readable storage medium is not a transitory signal per se, and where the program instructions are executable by a processor to cause the processor to perform a method including identifying, by the processor, features found in at least one data instance, applying, by the processor, principal component analysis (PCA) to a dataset defined by a plurality of data instances including the at least one data instance and features corresponding to the at least one data instance to create at least one principal component for the at least one data instance, identifying, by the processor for the at least one data instance, a subset of at least one principal component, the subset indicating at least one principal component that is determined to be salient for the at least one data instance, determining, by the processor for the at least one data instance, a subset of the features, based on the subset of the principal components for the at least one data instance, the subset of the features indicating features that are determined to be salient for the at least one data instance, and performing, by the processor, one or more actions associated with the at least one data instance, utilizing the subset of the features determined to be salient for the at least one data instance.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 10 illustrates an exemplary metagenomics dataset, in accordance with one embodiment of the present invention.

DETAILED DESCRIPTION

Figure 1:
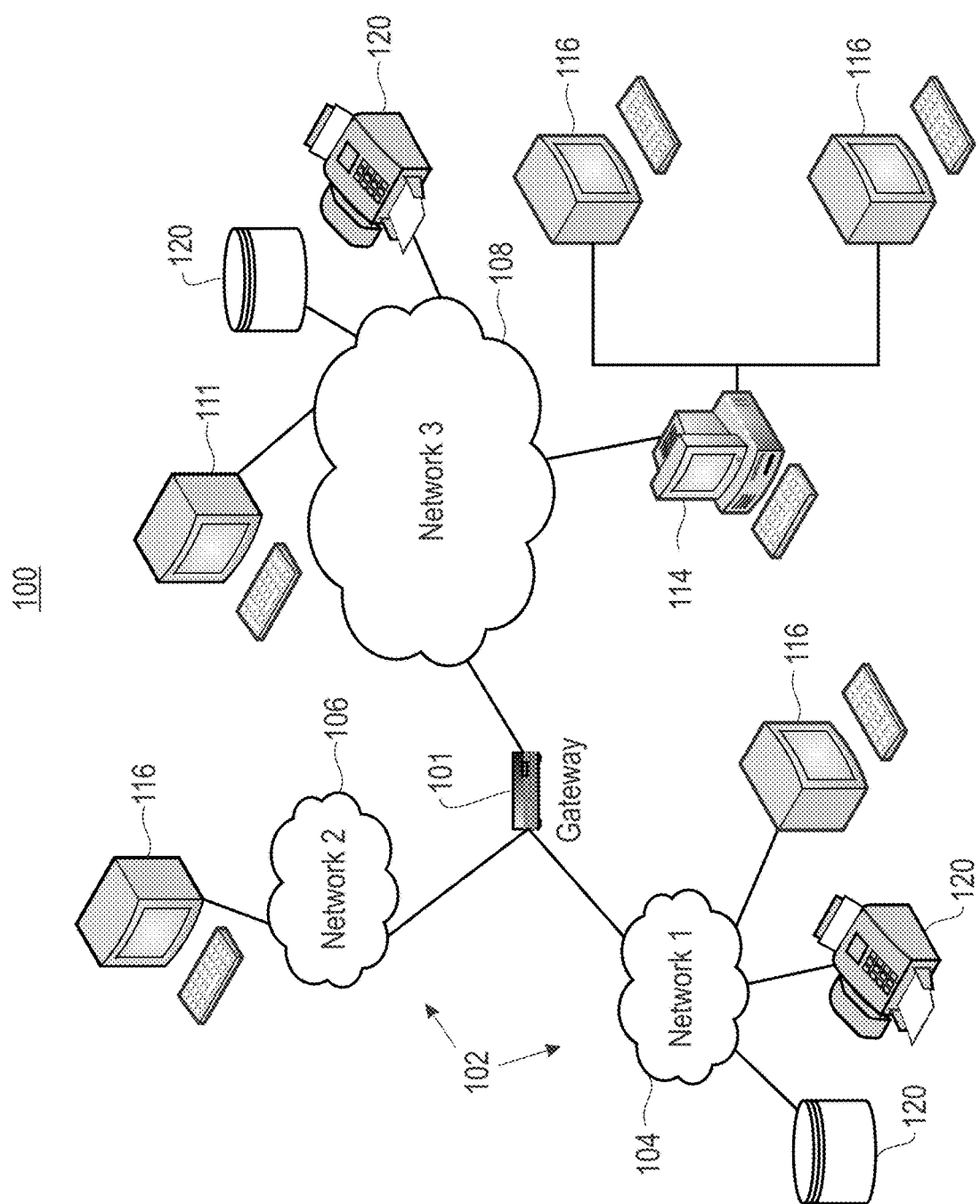
FIG. 1 illustrates a network architecture, in accordance with one embodiment of the present invention.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following description discloses several preferred embodiments of systems, methods and computer program products for identifying salient features for instances of data.

In one general embodiment, a computer-implemented method includes identifying principal components for a dataset defined by data instances and features corresponding to the data instances, identifying, for at least one of the data instances, at least some of the principal components, wherein the identified principal components are determined to be salient for said at least one data instance, and determining, for said at least one of the data instances, one or more salient features corresponding to the identified salient principal components.

In another general embodiment, a computer program product for identifying salient features for instances of data includes a computer readable storage medium having program instructions embodied therewith, where the computer readable storage medium is not a transitory signal per se, and where the program instructions are executable by a processor to cause the processor to perform a method including identifying, by the processor, principal components for a dataset defined by data instances and features corresponding to the data instances, identifying, by the processor for at least one of the data instances, at least some of the principal components, wherein the identified principal components are determined to be salient for said at least one data instance, and determining, by the processor for said at least one of the data instances, one or more salient features corresponding to the identified salient principal components.

In another general embodiment, a system includes a processor, and logic integrated with the processor, executable by the processor, or integrated with and executable by the processor, where the logic is configured to identify principal components for a dataset defined by data instances and features corresponding to the data instances, identify, for at least one of the data instances, at least some of the principal components, wherein the identified principal components are determined to be salient for said at least one data instance, and determine, for said at least one of the data instances, one or more salient features corresponding to the identified salient principal components.

In another general embodiment, a computer-implemented method includes identifying features found in at least one data instance, applying principal component analysis (PCA) to a dataset defined by a plurality of data instances including the at least one data instance and features corresponding to the at least one data instance to create at least one principal component for the at least one data instance, identifying, for the at least one data instance, a subset of the at least one principal component, the subset indicating at least one principal component that is determined to be salient for the at least one data instance, determining, for the at least one data instance, a subset of the features, based on the subset of the principal components for the at least one data instance, the subset of the features indicating features that are determined to be salient for the at least one data instance, and performing one or more actions associated with the at least one data instance, utilizing the subset of the features determined to be salient for the at least one data instance.

In another general embodiment, a computer program product for identifying salient features for instances of data includes a computer readable storage medium having program instructions embodied therewith, where the computer readable storage medium is not a transitory signal per se, and where the program instructions are executable by a processor to cause the processor to perform a method including identifying, by the processor, features found in at least one data instance, applying, by the processor, principal component analysis (PCA) to a dataset defined by a plurality of data instances including the at least one data instance and features corresponding to the at least one data instance to create at least one principal component for the at least one data instance, identifying, by the processor for the at least one data instance, a subset of the at least one principal component, the subset indicating at least one principal component that is determined to be salient for the at least one data instance, determining, by the processor for the at least one data instance, a subset of the features, based on the subset of the principal components for the at least one data instance, the subset of the features indicating features that are determined to be salient for the at least one data instance, and performing, by the processor, one or more actions associated with the at least one data instance, utilizing the subset of the features determined to be salient for the at least one data instance.

FIG. 1 illustrates an architecture 100, in accordance with one embodiment. As shown in FIG. 1, a plurality of remote networks 102 are provided including a first remote network 104 and a second remote network 106. A gateway 101 may be coupled between the remote networks 102 and a proximate network 108. In the context of the present architecture 100, the networks 104, 106 may each take any form including, but not limited to a LAN, a WAN such as the Internet, public switched telephone network (PSTN), internal telephone network, etc.

In use, the gateway 101 serves as an entrance point from the remote networks 102 to the proximate network 108. As such, the gateway 101 may function as a router, which is capable of directing a given packet of data that arrives at the gateway 101, and a switch, which furnishes the actual path in and out of the gateway 101 for a given packet.

Further included is at least one data server 114 coupled to the proximate network 108, and which is accessible from the remote networks 102 via the gateway 101. It should be noted that the data server(s) 114 may include any type of computing device/groupware. Coupled to each data server 114 is a plurality of user devices 116. User devices 116 may also be connected directly through one of the networks 104, 106, 108. Such user devices 116 may include a desktop computer, lap-top computer, hand-held computer, printer or any other type of logic. It should be noted that a user device 111 may also be directly coupled to any of the networks, in one embodiment.

A peripheral 120 or series of peripherals 120, e.g., facsimile machines, printers, networked and/or local storage units or systems, etc., may be coupled to one or more of the networks 104, 106, 108. It should be noted that databases and/or additional components may be utilized with, or integrated into, any type of network element coupled to the networks 104, 106, 108. In the context of the present description, a network element may refer to any component of a network.

According to some approaches, methods and systems described herein may be implemented with and/or on virtual systems and/or systems which emulate one or more other systems, such as a UNIX system which emulates an IBM z/OS environment, a UNIX system which virtually hosts a MICROSOFT WINDOWS environment, a MICROSOFT WINDOWS system which emulates an IBM z/OS environment, etc. This virtualization and/or emulation may be enhanced through the use of VMWARE software, in some embodiments.

In more approaches, one or more networks 104, 106, 108, may represent a cluster of systems commonly referred to as a "cloud." In cloud computing, shared resources, such as processing power, peripherals, software, data, servers, etc., are provided to any system in the cloud in an on-demand relationship, thereby allowing access and distribution of services across many computing systems. Cloud computing typically involves an Internet connection between the systems operating in the cloud, but other techniques of connecting the systems may also be used.

Figure 2:
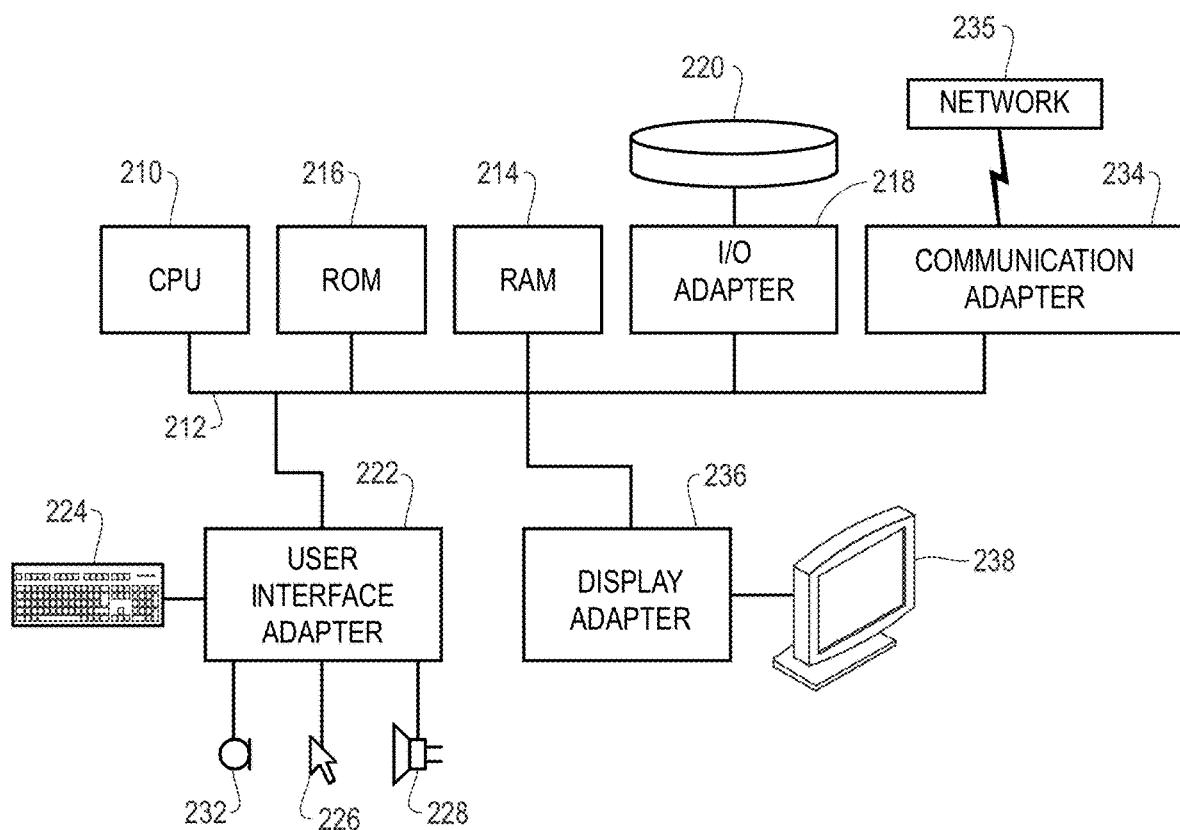
FIG. 2 shows a representative hardware environment that may be associated with the servers and/or clients of FIG. 1, in accordance with one embodiment of the present invention.

FIG. 2 shows a representative hardware environment associated with a user device 116 and/or server 114 of FIG. 1, in accordance with one embodiment. Such a figure illustrates a typical hardware configuration of a workstation having a central processing unit 210, such as a microprocessor, and a number of other units interconnected via a system bus 212.

The workstation shown in FIG. 2 includes a Random Access Memory (RAM) 214, Read Only Memory (ROM) 216, an I/O adapter 218 for connecting peripheral devices such as disk storage units 220 to the bus 212, a user interface adapter 222 for connecting a keyboard 224, a mouse 226, a speaker 228, a microphone 232, and/or other user interface devices such as a touch screen and a digital camera (not shown) to the bus 212, communication adapter 234 for connecting the workstation to a communication network 235 (e.g., a data processing network) and a display adapter 236 for connecting the bus 212 to a display device 238.

The workstation may have resident thereon an operating system such as the Microsoft Windows® Operating System (OS), a MAC OS, a UNIX OS, etc. It will be appreciated that a preferred embodiment may also be implemented on platforms and operating systems other than those mentioned. A preferred embodiment may be written using XML, C, and/or C++ language, or other programming languages, along with an object oriented programming methodology. Object oriented programming (OOP), which has become increasingly used to develop complex applications, may be used.

Figure 3:
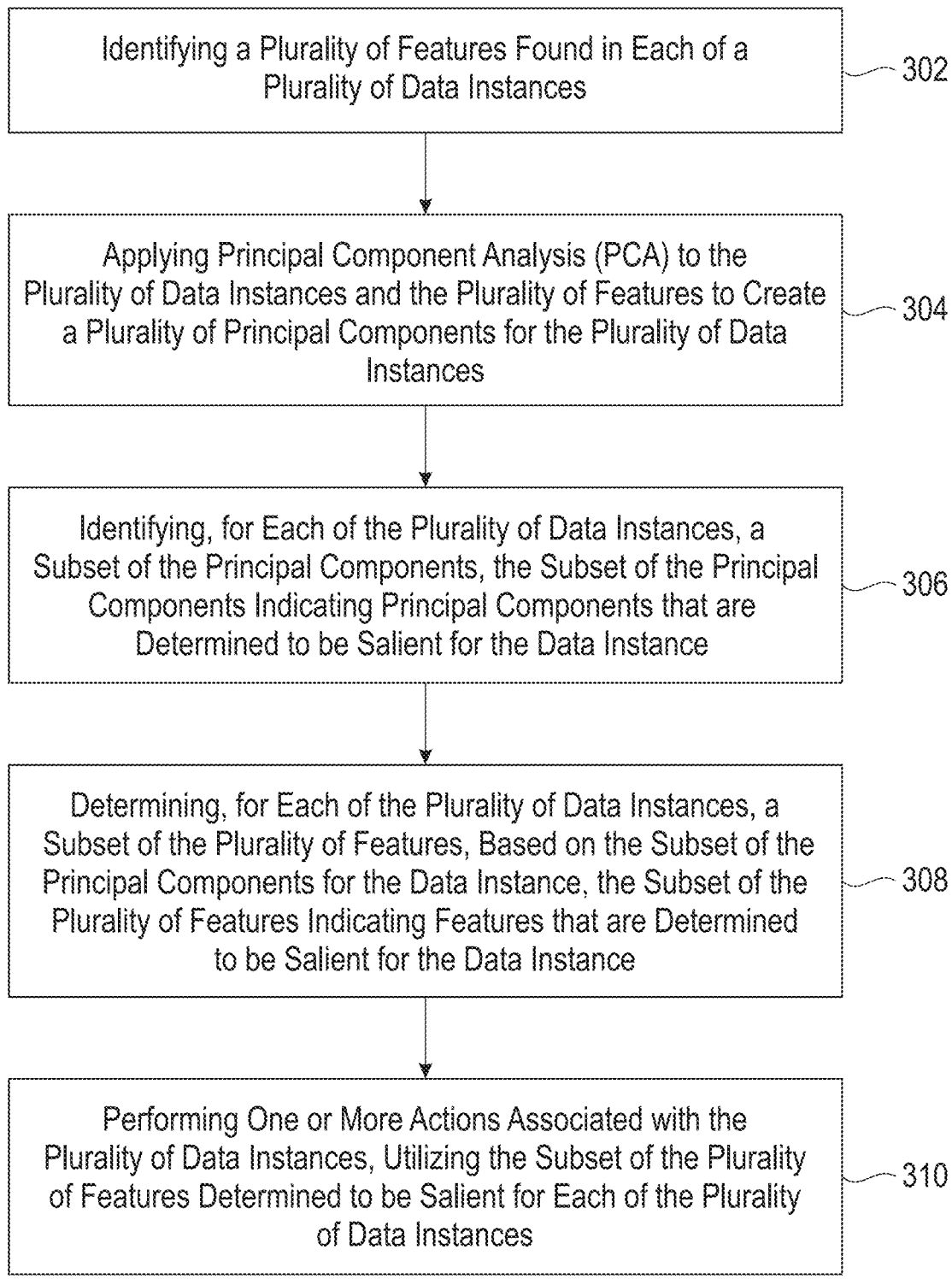
FIG. 3 illustrates a method for identifying salient features for instances of data, in accordance with one embodiment of the present invention.

Now referring to FIG. 3, a flowchart of a method 300 is shown according to one embodiment. The method 300 may be performed in accordance with the present invention in any of the environments depicted in FIGS. 1 and 2, among others, in various embodiments. Of course, more or less operations than those specifically described in FIG. 3 may be included in method 300, as would be understood by one of skill in the art upon reading the present descriptions.

Each of the steps of the method 300 may be performed by any suitable component of the operating environment. For example, in various embodiments, the method 300 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 300. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 3, method 300 may initiate with operation 302, where a plurality of features found in each of a plurality of data instances are identified. In one embodiment, each of the plurality of data instances may include a value for all of the plurality of features. For example, each of the plurality of data instances may be associated with an individual and may include distinct features such as height, weight, age, etc. In another example, each of the plurality of data instances may be associated with an automobile and may include distinct features such as make, model, year, etc.

Additionally, in one embodiment, each of the plurality of features may possibly be correlated with each of the other features. In another embodiment, each of the plurality of features may be included within a set of features for the plurality of data instances. In yet another embodiment, each of the plurality of data instances may include one or more observations. In still another embodiment, each of the plurality of data instances may have an observed value for each of the plurality of features (e.g., a height value, a weight value, etc.).

Further, in one embodiment, each of the plurality of data instances may be high-dimensional. For example, a number of the plurality of features shared by each of the plurality of data instances may exceed a predetermined threshold. In another embodiment, the plurality of data instances may include internet-of-things (IoT) data. For example, the plurality of data instances (and associated plurality of features) may include data acquired in an IoT environment (e.g., utilizing one or more smart appliances, etc.).

Further still, method 300 may proceed with operation 304, where principal component analysis (PCA) is applied to the plurality of data instances and the plurality of features to create a plurality of principal components for the plurality of data instances. In one embodiment, each of the principal components is considered a linearly uncorrelated variable created by applying the PCA. In another embodiment, applying PCA may include applying, for all of the plurality of data instances, an orthogonal transformation to the observed values for each of the plurality of features for the data instance to create transformed values for all of the plurality of principal components for the data instance.

For example, a principal component PC may include a weighted linear combination of features X and Y, as follows: $PC = \alpha X + \beta Y$, where $\alpha$ and $\beta$ are weight values. In another embodiment, the PCA may include classical PCA, or robust PCA. In yet another embodiment, the PCA may include eigenvalue decomposition or economical SVD.

Also, method 300 may proceed with operation 306, where for each of the plurality of data instances, a subset of the principal components is identified, the subset of the principal components indicating principal components that are determined to be salient for the data instance. In one embodiment, for each of the plurality of data instances, the subset of the principal components that are determined to be salient for the data instance may be identified by analyzing the data instance with respect to the principal components.

In addition, in one embodiment, for each of the plurality of data instances, the subset of the principal components that are determined to be salient for the data instance may include principal components that are determined to best characterize the data instance when compared to the other principal components. In another embodiment, each of the plurality of data instances may be analyzed individually, and a subset of the principal components may be determined to be salient for each data instance individually. In yet another embodiment, the subset of the principal components may include a predetermined number of the linearly uncorrelated values, a predetermined percentage of the linearly uncorrelated values, etc.

Furthermore, in one embodiment, identifying the subset of the principal components for a data instance may include determining an absolute value of all transformed values for each of the plurality of principal components for the data instance. For example, all transformed values for each of the plurality of principal components may be determined for a data instance. In another example, an absolute value may be determined for these transformed values (these may be called "absolute transformed values").

Further still, in one embodiment, identifying the subset of the principal components for a data instance may include selecting a predetermined number of principal components for the data instance that have the largest absolute transformed values for the data instance. For example, all of the principal components for a data instance may be ranked according to a corresponding absolute transformed value for the data instance. In another example, a first principal component with a first corresponding absolute transformed value for the data instance may be ranked higher than a second principal component with a second corresponding absolute transformed value for the data instance, where the first corresponding absolute transformed value is greater than the second corresponding absolute transformed value. In yet another example, a predetermined number of the ranked principal components may be selected for the data instance, starting with a principal component with a highest corresponding absolute transformed value for the data instance.

Also, method 300 may proceed with operation 308, where for each of the plurality of data instances, a subset of the plurality of features is determined, based on the subset of the principal components for the data instance, the subset of the plurality of features indicating features that are determined to be salient for the data instance. In one embodiment, for each of the plurality of data instances, the features that are determined to be salient for the data instance may include features that are determined to best characterize the data instance when compared to the other features. In another embodiment, each of the principal components may be created via PCA from two or more features.

Additionally, in one embodiment, each of the principal components may include a linear combination of two or more features, where each feature within the linear combination may be associated with a predetermined weight. For example, a principal component PC may include a weighted linear combination of features X and Y, as follows: $PC=\alpha X+\beta Y$, where $\alpha$ and $\beta$ are weight values. In another embodiment, the two or more features may be weighted during the application of PCA to the plurality of data instances and a plurality of features for the plurality of data instances to create the plurality of principal components for the plurality of data instances.

Further, in one embodiment, for each of the subset of the principal components identified for a data instance, the weights used to create the principal component via PCA may be identified. For example, each of the weights may be associated with a single feature. In another embodiment, an absolute value of all weights may be determined (these may be called "absolute weight values") and sorted in decreasing order, and a predetermined number of the largest absolute weight values R may be identified for each principal component to create the subset of the plurality of features. In the above example, the absolute values of $\alpha$ and $\beta$ may be determined.

Further still, in one embodiment, the features associated with the largest absolute weight values may be selected as the salient features for the principal component. This may be performed for each principal component of the subset of the principal components for the data instance to determine the subset of the plurality of features for the data instance. In the above example, if $\alpha>\beta$, then X may be selected instead of Y as the salient feature for the principal component PC Likewise, if $\alpha<\beta$, then Y may be selected instead of X as the salient feature for the principal component PC. In one embodiment, for each principal component of the subset of the principal components for the data instance, the set of associated salient features may overlap. In response, overlapping features may be prioritized as being more salient than other non-overlapping features.

Also, method 300 may proceed with operation 310, where one or more actions associated with the plurality of data instances are performed, utilizing the subset of the plurality of features determined to be salient for each of the plurality of data instances. In one embodiment, performing one or more actions associated with the plurality of data instances may include labeling each of the plurality of data instances with its corresponding subset of the plurality of features, or using the same label (if available) as labeled data instances with a similar subset of plurality of salient features. In another embodiment, performing one or more actions associated with the plurality of data instances may include compressing the plurality of data instances, utilizing the corresponding subset of the plurality of features for each data instance.

In addition, in one embodiment, performing one or more actions associated with the plurality of data instances may include determining one or more anomalies within the plurality of data instances, utilizing the subset of the plurality of features determined for each of the plurality of data instances. For example, data instances within the plurality of data instances having salient features different from the majority of data instances may be identified as anomalous.

Furthermore, in one embodiment, performing one or more actions associated with the plurality of data instances may include training a machine learning apparatus, utilizing the plurality of data instances and the subset of the plurality of salient features determined for each of the plurality of data instances. For example, the plurality of data instances and the subset of the plurality of salient features determined for each of the plurality of data instances may be used as input to the machine learning apparatus to assist with one or more operations (e.g., classification, etc.).

In this way, when given data instances having a large number of features, these features may be analyzed to determine a smaller set of features that best characterize each data instance. This reduced set of salient features may be stored in association with each data instance instead of all available features for the data instance, which reduces the amount of metadata data to be stored with the data instances, and which in turn increases the available storage space of computing and storage devices performing the metadata storage, which may improve the performance of such devices.

Additionally, by reducing a large number of features to a smaller set of salient features for a data instance, training utilizing the data instance may be improved. For example, a machine learning apparatus may be trained with a data instance and the smaller set of salient features, instead of all features for the data instance. This may reduce the amount of data needed to be processed during training, as well as noise and errors, which may improve performance and accuracy of a computing device performing the training. By using the most salient features of a data instance during training, results of the trained machine learning apparatus may be improved as well when compared to training with all features of a data instance, which may improve a performance of the trained machine learning apparatus.

Further, salient features may be used for each data instance during compression of the data instance, which may improve the compression and later reconstruction of the plurality of data instances, saving storage and memory needed to store data instances.

In general, when data instances have a large group of associated features, salient features may be identified within that large group, and processing and storage resources may then be applied to these salient features in order to maximize an effect of such actions.

Figure 4:
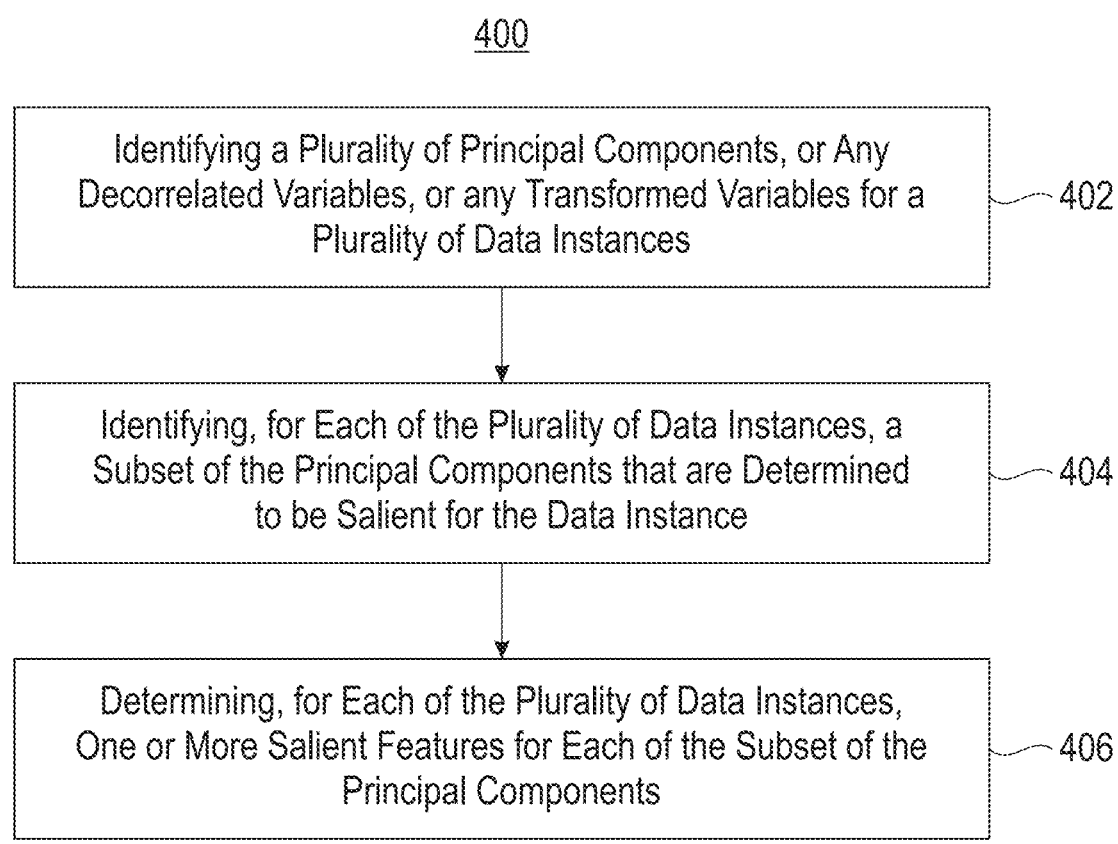
FIG. 4 illustrates a method for identifying salient features for a plurality of data instances, in accordance with one embodiment of the present invention.

Now referring to FIG. 4, a flowchart of a method 400 for identifying salient features for a plurality of data instances is shown according to one embodiment. The method 400 may be performed in accordance with the present invention in any of the environments depicted in FIGS. 1 and 2, among others, in various embodiments. Of course, greater or fewer operations than those specifically described in FIG. 4 may be included in method 400, as would be understood by one of skill in the art upon reading the present descriptions.

Each of the steps of the method 400 may be performed by any suitable component of the operating environment. For example, in various embodiments, the method 400 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 400. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 4, method 400 may initiate with operation 402, where a plurality of principal components, or any decorrelated variables, or any transformed variables, are identified for a plurality of data instances. In one embodiment, the principal components may be a result of applying PCA to a plurality of data instances and an associated plurality of features for those data instances.

Additionally, method 400 may proceed with operation 404, where for each of the plurality of data instances, a subset of the principal components that are determined to be salient for the data instance are identified. In one embodiment, the subset may be determined by selecting a predetermined number of the principal components, based on an absolute value of the principal components corresponding to the data instance. For example, the subset may be determined by selecting a predetermined number of the principal components, based on a principle component's contribution to the distance of an observation from the origin in the principal components space. In another embodiment, the principal components may be ranked based on an absolute value of the principal components corresponding to the data instance. In yet another embodiment, a predetermined number of the ranked principal components may be selected, starting with the largest absolute transformed value.

Further, method 400 may proceed with operation 406, where for each of the plurality of data instances, one or more salient features for each of the subset of the principal components are determined for each of the plurality of data instances. In one embodiment, the one or more salient features may be determined by selecting a predetermined number of the features for each of the plurality of data instances, based on an absolute value of a weight value associated with each feature. In another embodiment, the weight value associated with each feature is applied during the application of PCA to the plurality of data instances and a plurality of features for the plurality of data instances to create the plurality of principal components for the plurality of data instances.

Further still, in one embodiment, for each principal component, the features used to create the principal component via PCA may be ranked based on an absolute value of the associated weight for the features used during PCA or other transformations. In another embodiment, a predetermined number of the features may be selected, starting with the highest absolute value of the associated weight for the feature.

Feature-Selection Method for Automatic Labeling and the Characterization of Salient Features of Observations/Samples/Data-Points for High-Dimensional Genomics & Metagenomics Data There are many fundamental methods in machine learning that rely on the identification of what characterizes an observation or a set of observations, such as:

Feature-selection
Identification of Salient-Features
Compression/Dimensionality-Reduction
Similarity-matching
Clustering
Automatic Labeling
Anomaly-detection
Distance-matrices
Jaccard-similarity Index However, there are no methods or systems available today that efficiently and accurately provide salient features characterizing a given observation.

Figure 5:
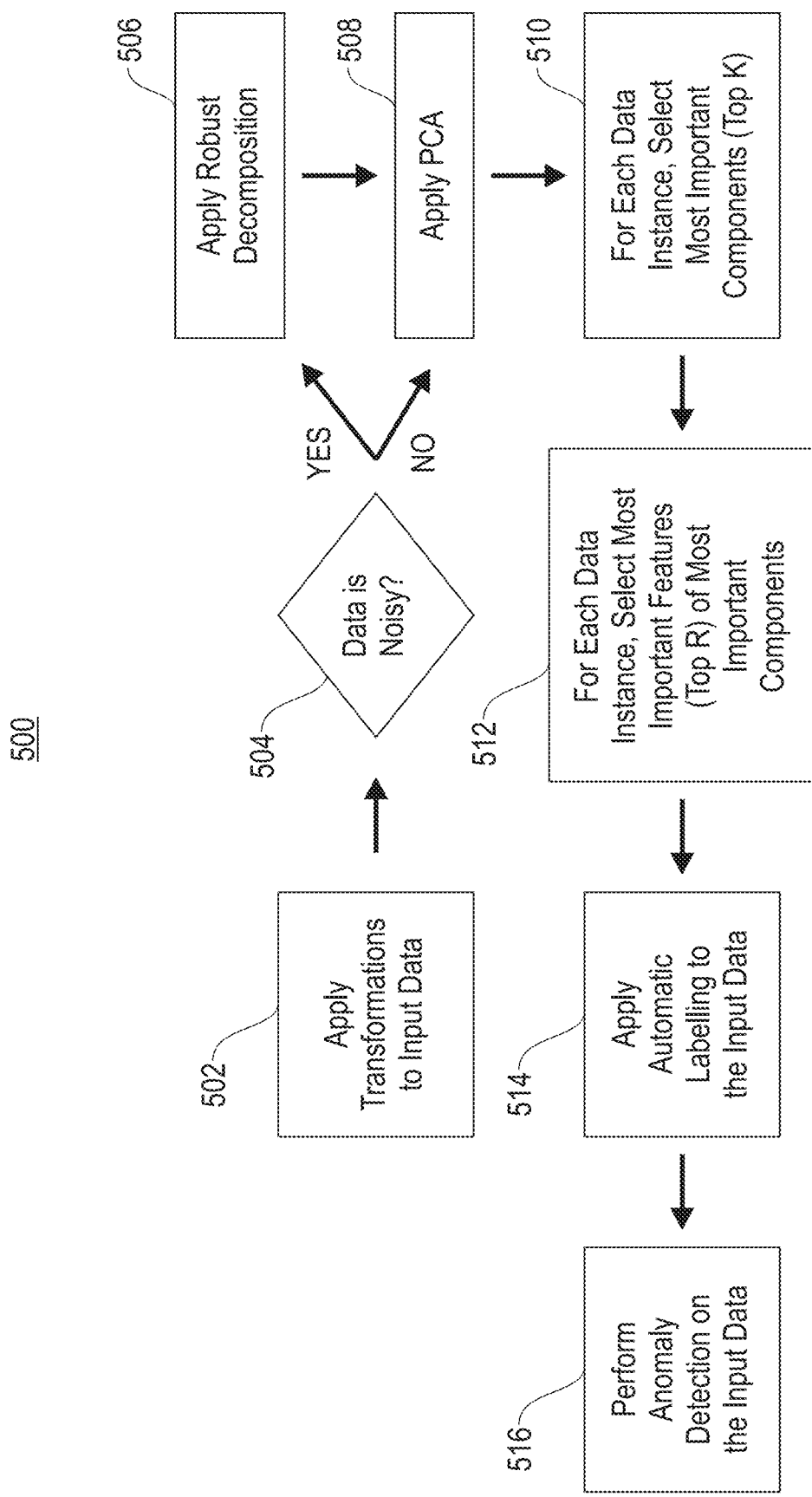
FIG. 5 illustrates a method for identifying salient features of input data, in accordance with one embodiment of the present invention.

Now referring to FIG. 5, a flowchart of a method 500 for identifying salient features of input data is shown according to one embodiment. The method 500 may be performed in accordance with the present invention in any of the environments depicted in FIGS. 1 and 2, among others, in various embodiments. Of course, more or less operations than those specifically described in FIG. 5 may be included in method 500, as would be understood by one of skill in the art upon reading the present descriptions.

Each of the steps of the method 500 may be performed by any suitable component of the operating environment. For example, in various embodiments, the method 500 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 500. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 5, method 500 may initiate with operation 502, where transformations are applied to input data. In one embodiment, the transformations may include one or more of normalization, standardization, isometric log ratio (ILR) transformation, etc. Additionally, method 500 may proceed with decision 504, where it is determined whether the input data are noisy. If it is determined in decision 504 that the input data are noisy, then method 500 may proceed with operation 506, where robust decomposition is applied to the input data, and method 500 may proceed with operation 508, where principal component analysis is applied to the input data.

If it is determined in decision 504 that the input data are not noisy, then method 500 may proceed with operation 508, where principal component analysis is applied to the input data without performing robust decomposition. Additionally, method 500 may proceed with operation 510, where for each data instance within the input data, the most important/salient components are selected. In one embodiment, a predetermined number of the highest absolute value principal components may be selected for each data instance within the input data.

Further, method 500 may proceed with operation 512, where for each data instance within the input data, the most important features of the most important components are selected. This may result in a determination of the most important/salient features for each data instance within the input data.

Further still, method 500 may proceed with operation 514, where automatic labelling is applied to the input data. In one embodiment, the data instances may be clustered based on the selected most important features, and each cluster may be labeled. In another embodiment, salient features associated with each cluster may be identified.

Also, method 500 may proceed with operation 516, where anomaly detection is performed on the input data. In one embodiment, anomalous features may be detected based on the selected most important features. In another embodiment, a database storing the input data may be updated, based on the anomalous features. For example, data instances that include anomalous features may be removed from the database. In yet another embodiment, the anomalous features may be reported, and not removed from the database. In still another embodiment, the anomalous features may be used to train one or more anomaly detection algorithms.

In this way, salient features may be determined for input data, which may assist in both automatic labelling and anomaly detection utilizing the input data.

In one embodiment, principal component analysis (PCA) is applied to data instances to de-correlate variables/features within the data instances. For example, PCA is a statistical procedure that uses an orthogonal transformation to convert a set of data instances having possibly correlated variables ([features/entities/coordinates] each of which takes on various numerical values) into a set of values of linearly uncorrelated variables/coordinates called principal components.

Figure 6:
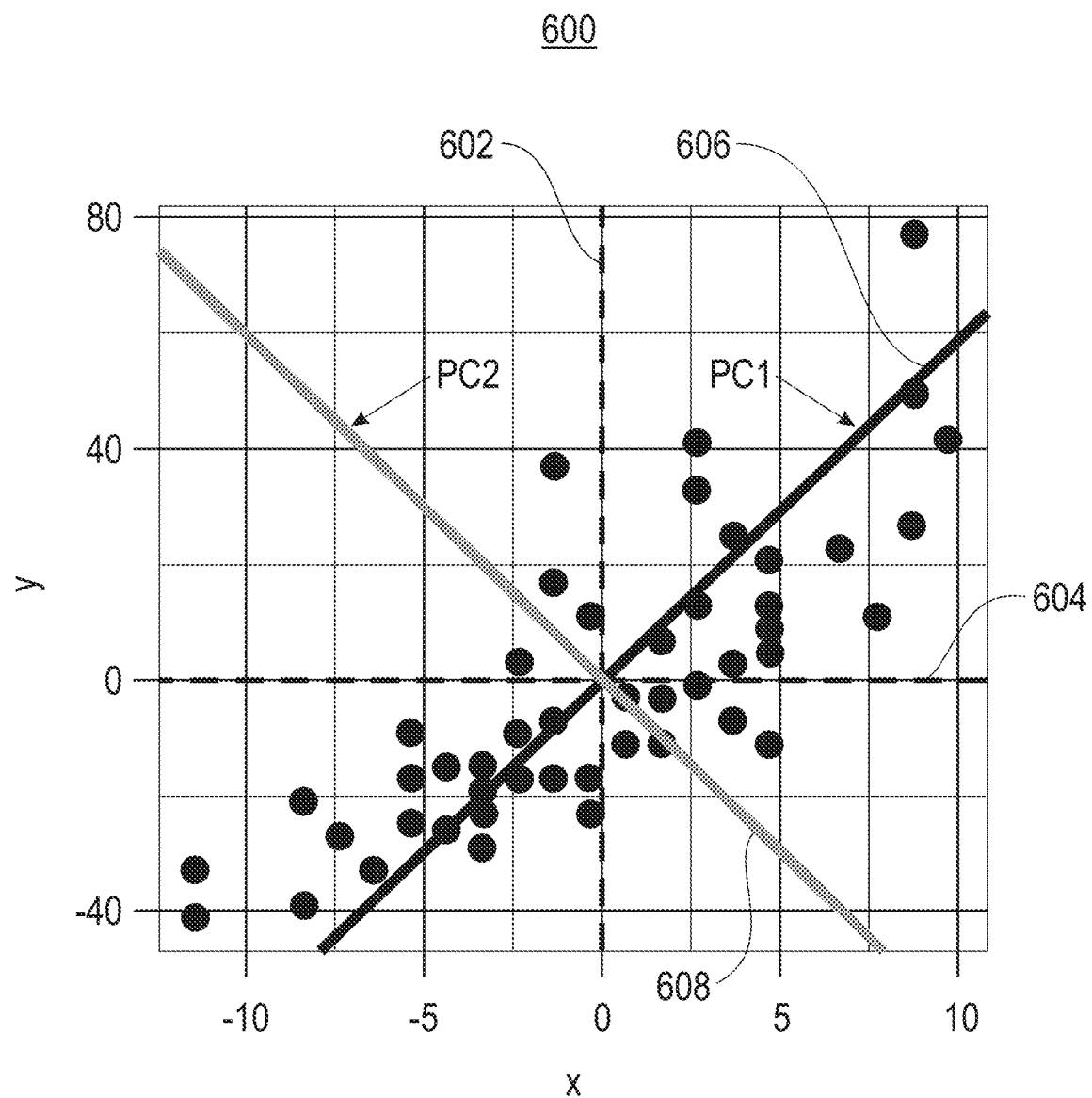
FIG. 6 illustrates an exemplary principal component analysis (PCA) implementation, in accordance with one embodiment of the present invention.

FIG. 6 illustrates an exemplary principal component analysis (PCA) implementation 600, according to one exemplary embodiment. As shown in FIG. 6, PCA is applied to the plurality of data instances and plurality of features; a first feature 602 (represented by the X-axis) and a second feature 604 (represented by the Y-axis) to create a first principal component (PC1) 606 and a second principal component (PC2) 608.

Figure 7:
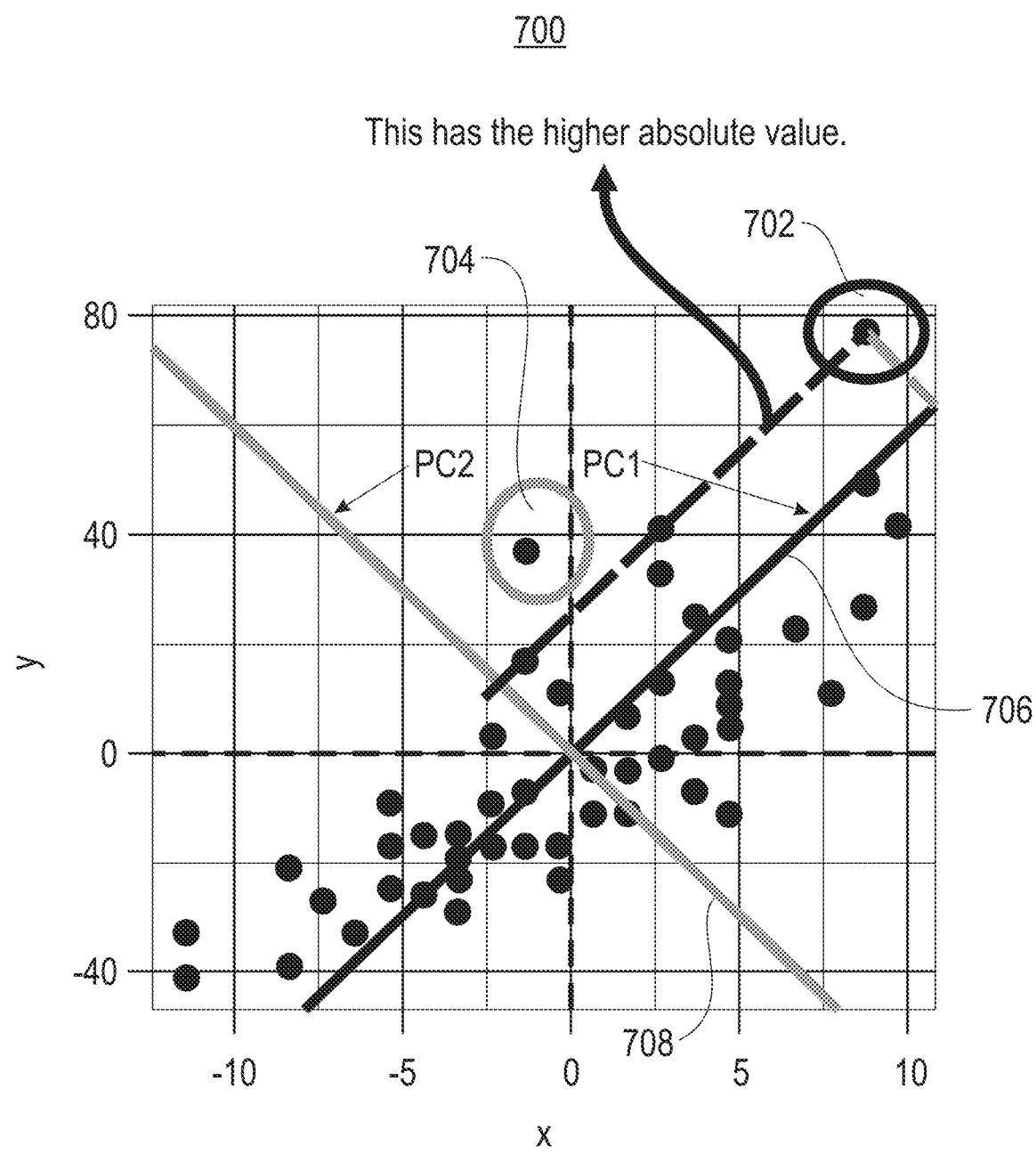
FIG. 7 illustrates the selection of a salient principal component for two data instances, in accordance with one embodiment of the present invention.

Additionally, in one embodiment, the most important principal components are determined individually for each data instance within a set. FIG. 7 illustrates the selection 700 of a salient principal component for two data instances 702 and 704, according to one exemplary embodiment. As shown, an absolute value for the PC1 component 706 of a first data instance 702 is compared to an absolute value for the PC2 component 708 of the first data instance 702. The absolute value of the PC1 component 706 is greater than the absolute value for the PC2 component 708 for the first data instance 702, and the PC1 component 706 is selected as the salient component for the first data instance 702 as a result.

Further, an absolute value for the PC1 component 706 of the second data instance 704 is compared to an absolute value for the PC2 component 708 of the second data instance 704. The absolute value of the PC1 component 706 is less than the absolute value for the PC2 component 708 for the second data instance 704, and the PC2 component 708 is selected as the salient component for the second data instance 704 as a result.

Further still, in one embodiment, once the top most important/critical components/coordinates per data instance are identified, the most important features for each data instance are determined by reverting back to the original coordinate space and selecting features based on the highest absolute value of their weights/contribution to the corresponding salient principal component/coordinate.

Figure 8:
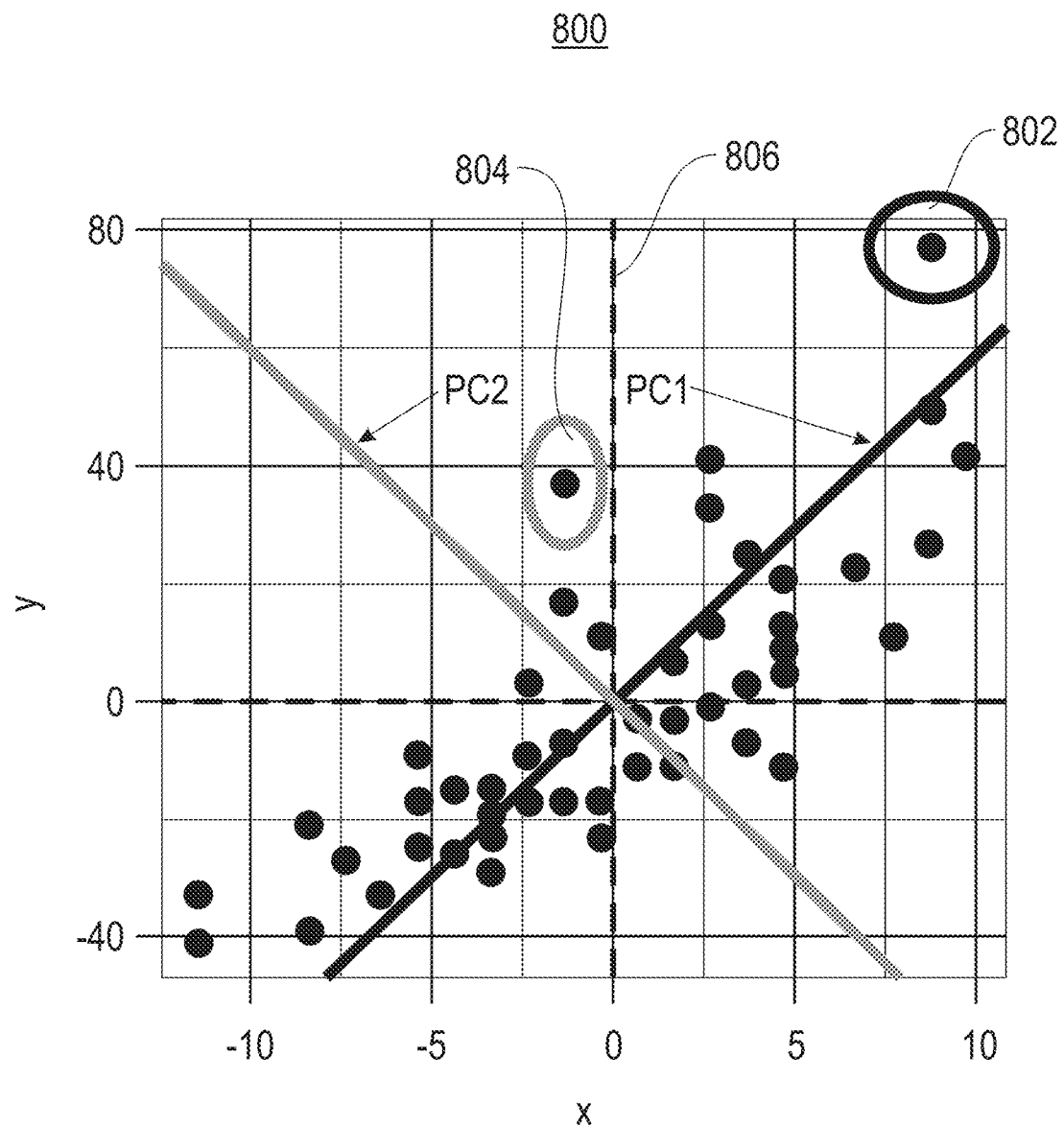
FIG. 8 illustrates the selection of a salient feature component for two data instances, in accordance with one embodiment of the present invention.

FIG. 8 illustrates the selection 800 of a salient feature component for two data instances 802 and 804, according to one exemplary embodiment. As shown, an absolute value for the X feature 806 of a first data instance 802 is compared to an absolute value for the Y feature 808 of the first data instance 802. The absolute value of the X feature 806 is greater than the absolute value for the Y feature 808 for the first data instance 802, and the X feature 806 is selected as the salient feature for the first data instance 802 as a result.

Also, an absolute value for the X feature 806 of the second data instance 804 is compared to an absolute value for the Y feature 808 of the second data instance 804. The absolute value of the X feature 806 is less than the absolute value for the Y feature 808 for the second data instance 804, and the Y feature 808 is selected as the salient feature for the second data instance 804 as a result.

In one embodiment, principal component analysis is applied to a dataset. Additionally, for each observation/sample, the most important principal components/coordinates are selected, based on the highest absolute values of the principal components/coordinates. Further, for each observation/sample and its corresponding most important principal component/coordinate, the most important features are selected based on the highest absolute values of their weights/contributions to the corresponding principal component/coordinate.

In another embodiment, salient features may be determined for metagenomics data. For example, starting from OTUs or a count matrix, where each row 'i' is a biological sample and each column is a feature (microbe), a necessary transformation is applied to obtain matrix 'X' (e.g. normalization, isometric log-ratio transformation, scaling/standardization, etc.).

If the data are noisy, robust decomposition is applied (e.g., using randomized SVD) and a low-rank component 'L' is used instead of the original matrix 'X'. PCA is applied to rotate the matrix into a new coordinate system with linearly independent features with zero correlation. For each observation/data-point 'i', the most important 'K' coordinates/principal components are identified.

For each observation/data-point 'i', the most important/salient 'R' features associated with each important/salient coordinate/principal component are identified to arrive at the set of salient features (K*R features). If automatic labeling is desired, in one embodiment a similarity metric (e.g. a Jaccard-index) is chosen and observations are clustered based on their salient features; then each cluster is labeled using the associated salient features (e.g., the intersection set of salient features associated with all observations in a given cluster is used). Or, if labels are available, the labels from labeled data instances within a given cluster may be used. If the data are already labeled, salient features associated with each class/label are identified (e.g., using the intersection set of salient features associated with all observations in a given cluster). This step is an example application of automatic-labeling.

If there are anomalous observations/data-points, associated salient features are identified, then the data are updated—these features that are associated with anomalies are then used by anomaly detection algorithms to detect anomalous samples. This is an example of an application of the invention for the discovery of anomalies of biological samples (e.g., to eliminate unsafe food products, etc.).

Figure 9:
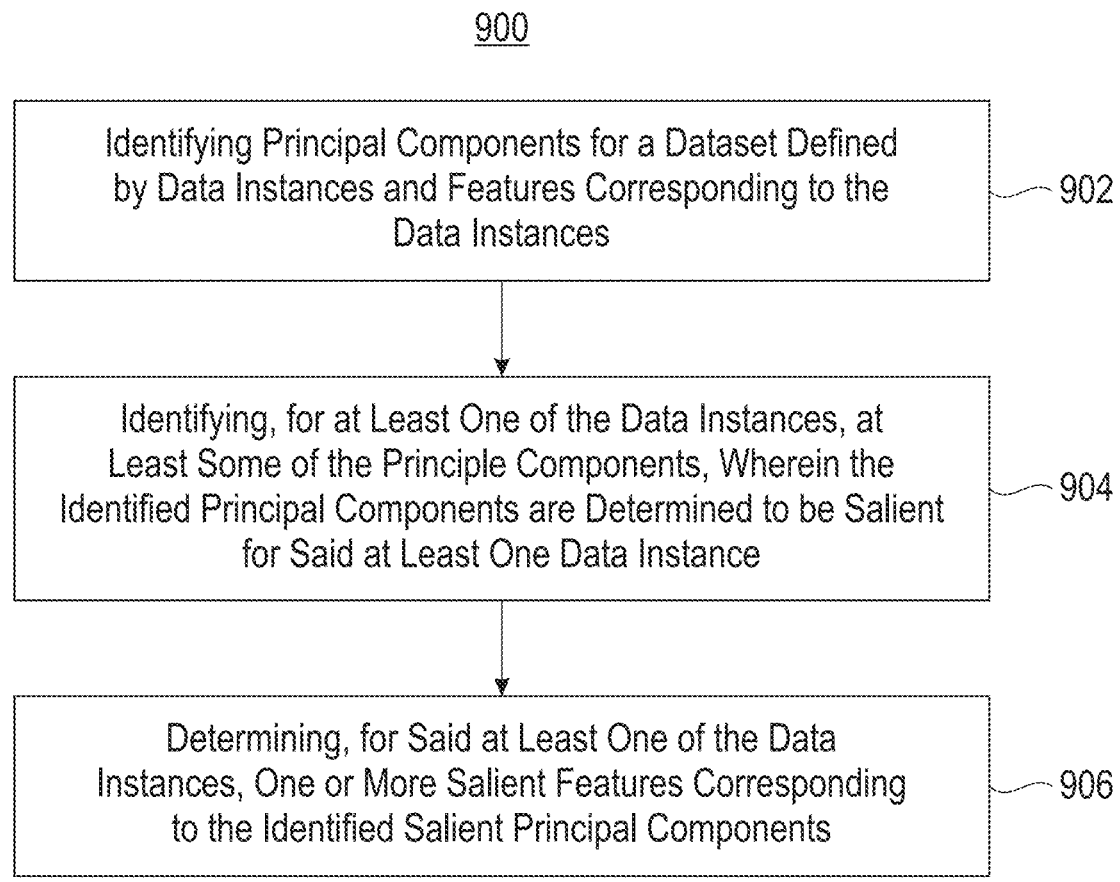
FIG. 9 illustrates another method for identifying salient features of input data, in accordance with one embodiment of the present invention.

Now referring to FIG. 9, a flowchart of another method 900 for identifying salient features of input data is shown according to one embodiment. The method 900 may be performed in accordance with the present invention in any of the environments depicted in FIGS. 1 and 2, among others, in various embodiments. Of course, more or less operations than those specifically described in FIG. 9 may be included in method 900, as would be understood by one of skill in the art upon reading the present descriptions.

Each of the steps of the method 900 may be performed by any suitable component of the operating environment. For example, in various embodiments, the method 900 may be partially or entirely performed by one or more servers, computers, or some other device having one or more processors therein. The processor, e.g., processing circuit(s), chip(s), and/or module(s) implemented in hardware and/or software, and preferably having at least one hardware component may be utilized in any device to perform one or more steps of the method 900. Illustrative processors include, but are not limited to, a central processing unit (CPU), an application specific integrated circuit (ASIC), a field programmable gate array (FPGA), etc., combinations thereof, or any other suitable computing device known in the art.

As shown in FIG. 9, method 900 may initiate with operation 902, where principal components are identified for a dataset defined by data instances and features corresponding to the data instances. Additionally, method 900 may proceed with operation 904, where at least some of the principal components are identified for at least one of the data instances, wherein the identified principal components are determined to be salient for said at least one data instance. Further, method 900 may proceed with operation 906, where one or more salient features corresponding to the identified salient principal components are determined for said at least one of the data instances.

In one embodiment, said identifying principal components comprises: applying principal component analysis (PCA) to the dataset. Additionally, in one embodiment, the salient principal components are determined in view of their absolute values for said at least one data instance. Further, in one embodiment, the number of salient principal components is preselected. Further still, in one embodiment, the salient principal components are selected in view of their magnitude.

In another embodiment, principal components may be deemed salient or important for a given data instance based on one or more additional criteria. For example, principal components may be deemed salient or important for a given data instance based on the absolute value of the principle components' scores for the given data instance, based on the principle components' contribution to the distance of a given data instance from the origin of the transformed space, or based on any variant thereof which may or may not apply additional transformations or normalizations.

Additionally, in one embodiment, the salient features are determined in view of the salient principal components. In another embodiment, the salient features are identified in view of the absolute value of their weights in the corresponding salient principal component. In yet another embodiment, a predetermined number of salient features is selected for at least one of the salient principal components.

Further, in one embodiment, the dataset includes microbiome data. In another embodiment, the dataset includes genome-wide association studies (GWAS) data. In yet another embodiment, the dataset includes medical imaging data. In still another embodiment, a cluster of data instances within the dataset are identified that share the one or more salient features, and a label is automatically applied to the cluster of data instances corresponding to the one or more salient features.

Further still, in one embodiment, one or more outliers are identified within the dataset, utilizing the one or more salient features. In one embodiment, the one or more outliers are removed from the dataset. In another embodiment, an amount of storage used to store the dataset is reduced by compressing the dataset using only the one or more salient features of the data instances in the dataset. In another embodiment, the one or more outliers may not be removed and may be reported. In still another embodiment, the one or more outliers may be used to train one or more algorithms (e.g., anomaly detection algorithms, etc.).

Automatic Labelling

In one embodiment, the determination of salient features for data instances may be used to perform automatic labeling (e.g., for medical images, etc.). For example, this determination of salient features is immediately applicable to solve a critical problem today—the problem of unlabeled data. Most data today is unlabeled and is not readily utilized.

By extracting salient features of data instances, one can identify clusters of data instances that share salient features and apply a label to them. In another embodiment, salient features could be used to generate labels. For example, one can use a subset of salient features as a label. Another way to generate labels for said clusters of unlabeled data instances is using a human in the loop model. For example, a human could generate labels based on only a small subset of data instances in each cluster.

In real world applications, usually, a small subset of data instances are labeled, in which case one can give a label to all data instances in a given cluster based on those labeled data instances. If a cluster contains labeled data instances that have different labels, a label can be chosen for the cluster based on a combination thereof, or based on the label with the highest frequency in that cluster, or any other method that would align with the application.

In this way, clusters of data instances may be generated that enable us to perform automatic labeling. Those clusters rely on identifying salient features of data instances which the implementations herein provide.

Performance Improvements

In one embodiment, the determination of salient features for data instances may be used to improve a quality of compression, minimize an amount of storage used to store compressed data, increase an efficiency of computations used to analyze compressed data, and increase a performance of pattern recognition and machine learning systems.

For example, when data instances are described and stored in terms of their salient features as shown herein, a higher quality of compression using PCA is enabled. This is demonstrated by lower reconstruction errors. Compressing data instances usually leads to loss of information. With our methods, our ability to reconstruct original signal and data instances before compression is critically improved. Enabling higher quality compression provides savings in storage and memory and higher accuracy of analytics on compressed data.

When data instances are compressed using their salient features, using the methods shown herein, both noise and errors are generally decreased in pattern recognition systems that utilize them. Additionally, the performance of downstream analysis and machine learning and artificial intelligence algorithms utilizing the compressed data is improved. Further, performing compression in terms of salient features enables efficient computation and savings on computation costs.

Clustering Methods

In one embodiment, the determination of salient features for data instances may be used to implement clustering methods for data analysis. For example, using the implementations shown herein, we are able to characterize data instances in terms of their salient features (e.g., features that are deemed most important). This enables us to focus on features that are most characterizing, which reduces noise by ignoring features that are deemed irrelevant.

In one example, in clustering algorithms, the goal is to group data instances that are most similar together. Representing data instances in terms of their salient features allows us to compare them more effectively, which in turn results in higher quality clustering.

High-Dimensional Data

In one embodiment, the determination of salient features for data instances may be applied to applications with high-dimensional, and in some cases, low-sample size data. For example, there are many real-world applications with high-dimensional and low-sample size data. This creates a challenge for statistical or machine learning models. When the dimensionality of data is high and the size of the data are small, we generally have underdetermined systems, which prevents us from utilizing the data for statistical or machine learning models.

Using the implementations herein, we effectively reduce the dimensionality of data instances using their salient features.

Genomics/Metagenomics Applications

Applications that generally have high-dimensional data include genomics and metagenomics applications (e.g., microbiome data, etc.). For example, a human microbiome could be used to detect and predict illness or disease. However, data instances, which are a collection of biological samples coming from different patients, are very high-dimensional leading to poor accuracy of prediction algorithms and our inability to pinpoint the cause of illness or disease to a given set of features, where features here are microbes.

With the implementations described herein, we can characterize these said biological samples, whether human microbiome, food samples, or any other biological samples, in terms of the most salient microbes or other associated features, enabling us to identify those features that are potentially causally related to observed phenomena, such as illness/disease, unsafe pathogenic or adulterated food or contaminated water, or any phenomena associated with biological samples.

When the dimensionality is reduced, we are also able to improve the accuracy of prediction and pattern recognition models.

Mapping Genotype to Phenotype

Applications that generally have high-dimensional data also include applications that rely on mapping genotypes to phenotypes. A "genotype" is an organism's full hereditary genetic information. A "phenotype" is an organism's actual observed properties, such as morphology, development, or behavior. The mapping of a set of genotypes to a set of phenotypes is sometimes referred to as a genotype-phenotype map. There is a rich source of data in genome-wide association studies (GWAS). The applications range from patient diagnostic tools, to drug efficacy, to addressing antibiotic resistance and understanding antimicrobial resistance (AMR), to CRISPR-Cas9, and many more. We discuss one example below, illustrating how our methods are applicable to GWAS.

Genome-Wide Association Studies (GWAS)

GWAS is used to analyze relationships and associations between genetic variants and observed traits. GWASs typically focus on associations between single-nucleotide polymorphisms (SNPs) and traits such as major human diseases. However, GWASs can also be applied to any other genetic variants and any other organisms.

Applying the implementations described herein to GWAS, we are able to extract patterns and associations more effectively, since data instances are characterized by the most salient features instead of all observed features, which can be high-dimensional. This may uncover critical patterns that lead to effective interventions and more accurate predictions or conclusions.

One shared aspect in the above applications is that data are generally high-dimensional and the sample size can be a lot smaller. When data instances are characterized by their salient features, we are able to uncover patterns that were not previously detectable and are able to remove unnecessary noise, thereby reducing errors and increasing accuracy and performance of statistical and machine learning models.

Anomaly Detection

In general, data instances are described by a shared set of features. By using the implementations described herein to describe data instances by their salient features instead of all features, we are able observe outliers (e.g., those data instances that have salient features that are different from the rest). This is particularly effective when data are high-dimensional. When data instances have, for example, over one thousand features, reducing that to only fifty salient features, for instance, would enable us to understand and analyze the data more effectively. The implementations described herein describe how to choose those fifty features in such a way that would characterize data instances with high fidelity and accuracy, since those features are the top most important and salient features.

Working Example Based on Metagenomics Data

In one embodiment, an Operational Taxonomic Unit (OTU) table is a table or matrix that provides an abundance of different OTUs (i.e. organisms) per each biological sample in a given metagenomics dataset. In this example, a data instance is a metagenomic biological sample and associated features are the OTUs.

Implementing an embodiment of our system and using a metagenomics dataset, we identify salient features (OTUs) associated with metagenomic data instances. These data instances are labeled based on whether contamination was present or not. Data instances that are contaminated had common salient features that are different from the rest of the data instances in the dataset. See FIG. 10 for an exemplary metagenomics dataset 1000 in which data instances 1 1002, 3 1004, and 9 1006 are labeled as having contamination. The top salient feature for all three was feature 532 1008. Looking at the abundance numbers, feature 532 1008 had zero abundance in all three data instances, and positive abundance for the rest.

This embodiment system example did not have access to contamination labels. However, it identified salient features for contaminated samples that were overlapping when compared to other contaminated samples and non-overlapping when compared to non-contaminated samples.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Moreover, a system according to various embodiments may include a processor and logic integrated with and/or executable by the processor, the logic being configured to perform one or more of the process steps recited herein. The processor may be of any configuration as described herein, such as a discrete processor or a processing circuit that includes many components such as processing hardware, memory, I/O interfaces, etc. By integrated with, what is meant is that the processor has logic embedded therewith as hardware logic, such as an application specific integrated circuit (ASIC), a FPGA, etc. By executable by the processor, what is meant is that the logic is hardware logic; software logic such as firmware, part of an operating system, part of an application program; etc., or some combination of hardware and software logic that is accessible by the processor and configured to cause the processor to perform some functionality upon execution by the processor. Software logic may be stored on local and/or remote memory of any memory type, as known in the art. Any processor known in the art may be used, such as a software processor module and/or a hardware processor such as an ASIC, a FPGA, a central processing unit (CPU), an integrated circuit (IC), a graphics processing unit (GPU), etc.

It will be clear that the various features of the foregoing systems and/or methodologies may be combined in any way, creating a plurality of combinations from the descriptions presented above.

It will be further appreciated that embodiments of the present invention may be provided in the form of a service deployed on behalf of a customer to offer service on demand.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
    identifying principal components for a plurality of data instances, based on the plurality of data instances and a plurality of features corresponding to the data instances;
    determining a salient subset of the principal components for each of at least one of the data instances, where each principal component of the salient subset includes one or more features each associated with a predetermined weight; and
    determining, for each of the at least one of the data instances, one or more salient features corresponding to the salient subset of the principal components determined for the data instance, utilizing the absolute value of all predetermined weights for all features of principal components within the salient subset.

2. The computer-implemented method of claim 1, wherein identifying the principal components includes applying principal component analysis (PCA) to the plurality of data instances and the plurality of features.

3. The computer-implemented method of claim 1, comprising:
    identifying a cluster of data instances that share one or more salient features; and
    applying a label to the cluster of data instances corresponding to the one or more salient features;
    wherein:
    each principal component of the salient subset of the principal components determined for each data instance includes a combination of two or more features, and
    determining the one or more salient features corresponding to the salient subset of the principal components determined for each data instance includes:
    sorting the absolute value of all predetermined weights for all features included within the salient subset of the principal components determined for the data instance, and
    selecting a predetermined number of the features.

4. The computer-implemented method of claim 1, wherein identifying the principal components for the plurality of data instances includes applying principal component analysis (PCA) to the plurality of data instances and the plurality of features to create the principal components for the plurality of data instances, where:
    each of the principal components is considered a linearly uncorrelated variable created by applying PCA, and
    applying PCA includes applying, for all of the plurality of data instances, an orthogonal transformation to observed values for each of the plurality of features for the data instance to create transformed values for all of the principal components for the data instance.

5. The computer-implemented method of claim 1, wherein determining the salient subset of the principal components includes, for each of the at least one of the data instances:
    determining an absolute value of all transformed values for each of the principal components for the data instance,
    ranking the principal components for the data instance according to the absolute value for the principal components, and
    selecting a predetermined number of the ranked principal components for the data instance, starting with a principal component having a highest corresponding absolute value.

6. The computer-implemented method of claim 1, wherein:
- each principal component of the salient subset of the principal components determined for the data instance includes a linear combination of two or more features,
- each feature within the linear combination is associated with a predetermined weight determined during an application of principal component analysis (PCA) to the plurality of data instances and the plurality of features to create the principal components for the plurality of data instances, and
- determining the one or more salient features corresponding to the salient subset of the principal components determined for the data instance includes:
- sorting by their absolute value all predetermined weights for all features included within the salient subset of the principal components determined for the data instance, and
- selecting a predetermined number of the features, based on their sorted weights.

7. The computer-implemented method of claim 1, wherein the principal components are ranked based on an absolute value of the principal components.

8. The computer-implemented method of claim 1, wherein identifying the principal components for the plurality of data instances includes applying principal component analysis (PCA) to the plurality of data instances and the plurality of features to create the principal components for the plurality of data instances, where:
- each of the principal components is considered a linearly uncorrelated variable created by applying PCA, and
- applying PCA includes applying, for all of the plurality of data instances, an orthogonal transformation to observed values for each of the plurality of features for the data instance to create transformed values for all of the principal components for the data instance;
- wherein determining the salient subset of the principal components includes, for each of the at least one of the data instances:
- determining an absolute value of all the transformed values for each of the principal components for the data instance,
- ranking the principal components for the data instance according to the absolute value for the principal components, and
- selecting a predetermined number of the ranked principal components for the data instance, starting with a principal component having a highest corresponding absolute value;
- wherein:
- each principal component of the salient subset of the principal components determined for the data instance includes a linear combination of two or more features,
- each feature within the linear combination is associated with a predetermined weight determined during the application of PCA to the plurality of data instances and the plurality of features to create the principal components for the plurality of data instances, and
- determining the one or more salient features corresponding to the salient subset of the principal components determined for the data instance includes:
- sorting by their absolute value all predetermined weights for all features included within the salient subset of the principal components determined for the data instance, and
- selecting a predetermined number of the features, based on their sorted weights.

9. The computer-implemented method of claim 1, wherein the plurality of data instances includes microbiome data.

10. The computer-implemented method of claim 1, wherein the plurality of data instances includes genome-wide association studies (GWAS) data.

11. The computer-implemented method of claim 1, wherein the plurality of data instances includes medical imaging data.

12. The computer-implemented method of claim 1, comprising:
- identifying a cluster of data instances that share one or more salient features; and
- automatically applying a label to the cluster of data instances corresponding to the one or more salient features.

13. The computer-implemented method of claim 1, comprising:
- identifying one or more outliers within the plurality of data instances, utilizing the one or more salient features; and
- performing one or more actions, utilizing the one or more outliers.

14. The computer-implemented method of claim 1, further comprising reducing an amount of storage used to store the plurality of data instances by compressing at least one of the plurality of data instances utilizing their one or more salient features.

15. A computer program product comprising one or more computer readable storage media, and program instructions collectively stored on the one or more computer readable storage media, the program instructions comprising instructions configured to cause one or more processors to perform a method comprising:
- identifying, by the one or more processors, principal components for a plurality of data instances, based on the plurality of data instances and a plurality of features corresponding to the data instances;
- determining, by the one or more processors, a salient subset of the principal components for each of at least one of the data instances, where each principal component of the salient subset includes one or more features each associated with a predetermined weight; and
- determining, by the one or more processors for each of the at least one of the data instances, one or more salient features corresponding to the salient subset of the principal components determined for the data instance, utilizing the absolute value of all predetermined weights for all features of principal components within the salient subset.

16. The computer program product of claim 15, wherein identifying the principal components for the plurality of data instances includes applying principal component analysis (PCA) to the plurality of data instances and the plurality of features to create the principal components for the plurality of data instances, where:
- each of the principal components is considered a linearly uncorrelated variable created by applying PCA, and
- applying PCA includes applying, for all of the plurality of data instances, an orthogonal transformation to observed values for each of the plurality of features for the data instance to create transformed values for all of the principal components for the data instance.

17. The computer program product of claim 15, wherein determining the salient subset of the principal components includes, for each of the at least one of the data instances:

determining an absolute value of all transformed values for each of the principal components for the data instance, ranking the principal components for the data instance according to the absolute value for the principal components, and selecting a predetermined number of the ranked principal components for the data instance, starting with a principal component having a highest corresponding absolute value.

18. The computer program product of claim 15, wherein:

each principal component of the salient subset of the principal components determined for the data instance includes a linear combination of two or more features, each feature within the linear combination is associated with a predetermined weight determined during an application of principal component analysis (PCA) to the plurality of data instances and the plurality of features to create the principal components for the plurality of data instances, and determining the one or more salient features corresponding to the salient subset of the principal components determined for the data instance includes:

sorting by their absolute value all predetermined weights for all features included within the salient subset of the principal components determined for the data instance, and selecting a predetermined number of the features, based on their sorted weights.

19. A system, comprising:

a processor; and logic integrated with the processor, executable by the processor, or integrated with and executable by the processor, the logic being configured to:

identify principal components for a plurality of data instances, based on the plurality of data instances and a plurality of features corresponding to the data instances;

determine a salient subset of the principal components for each of at least one of the data instances, where each principal component of the salient subset includes one or more features each associated with a predetermined weight; and determine, for each of the at least one of the data instances, one or more salient features corresponding to the salient subset of the principal components determined for the data instance, utilizing the absolute value of all predetermined weights for all features of principal components within the salient subset.

20. A computer-implemented method, comprising:

identifying principal components for a plurality of data instances, based on the plurality of data instances and a plurality of features corresponding to the data instances;

determining a salient subset of the principal components for each of at least one of the data instances, where each of the salient subset of the principal components determined for the data instance includes a linear combination of two or more features, and each feature within the linear combination is associated with a predetermined weight determined during an application of principal component analysis (PCA) to the plurality of data instances and the plurality of features to create the principal components for the plurality of data instances;

determining, for each of the at least one of the data instances, one or more salient features corresponding to the salient subset of the principal components determined for the data instance, including:

sorting by their absolute value all predetermined weights for all features included within the salient subset of the principal components determined for the data instance, and selecting a predetermined number of the features, based on their sorted weights;

identifying a cluster of data instances that share one or more salient features; and automatically applying a label to the cluster of data instances corresponding to the one or more salient features.

21. The computer-implemented method of claim 20, wherein the plurality of data instances includes microbiome data.

22. The computer-implemented method of claim 20, wherein the plurality of data instances includes genome-wide association studies (GWAS) data.

23. The computer-implemented method of claim 20, wherein the plurality of data instances includes medical imaging data.

24. A computer program product comprising one or more computer readable storage media, and program instructions collectively stored on the one or more computer readable storage media, the program instructions comprising instructions configured to cause one or more processors to perform a method comprising:

identifying, by the one or more processors, principal components for a plurality of data instances, based on the plurality of data instances and a plurality of features corresponding to the data instances;

determining, by the one or more processors, a salient subset of the principal components for each of at least one of the data instances, where each of the salient subset of the principal components determined for the data instance includes a linear combination of two or more features, and each feature within the linear combination is associated with a predetermined weight determined during an application of principal component analysis (PCA) to the plurality of data instances and the plurality of features to create the principal components for the plurality of data instances;

determining, by the one or more processors for each of the at least one of the data instances, one or more salient features corresponding to the salient subset of the principal components determined for the data instance, including:

sorting, by the one or more processors, by their absolute value all predetermined weights for all features included within the salient subset of the principal components determined for the data instance, and selecting, by the one or more processors, a predetermined number of the features, based on their sorted weights;

identifying, by the one or more processors, a cluster of data instances that share one or more salient features; and automatically applying, by the one or more processors, a label to the cluster of data instances corresponding to the one or more salient features.

* * * * *